United States Patent
Mennen (10) Patent No.: US 9,890,115 B2
(45) Date of Patent: Feb. 13, 2018

(54) UREA FINISHING METHOD

(71) Applicant: Stamicarbon B.V., Sittard (NL)

(72) Inventor: Johannes Henricus Mennen, Sittard (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 14/127,962

(22) PCT Filed: Oct. 12, 2012

(86) PCT No.: PCT/NL2012/050715
§ 371 (c)(1),
(2) Date: Dec. 19, 2013

(87) PCT Pub. No.: WO2013/055219
PCT Pub. Date: Apr. 18, 2013

(65) Prior Publication Data
US 2015/0026943 A1     Jan. 29, 2015

(30) Foreign Application Priority Data

Oct. 14, 2011 (EP) ..................................... 11185307

(51) Int. Cl.
*C07C 273/16* (2006.01)
*C07C 273/14* (2006.01)
(Continued)

(52) U.S. Cl.
CPC .............. *C07C 273/16* (2013.01); *B01J 2/22* (2013.01); *B01J 2/30* (2013.01); *B29C 43/006* (2013.01);
(Continued)

(58) Field of Classification Search
CPC .......... B01J 2/22; B29C 43/006; B29C 43/00; B29C 43/003; B29K 2075/02;
(Continued)

(56) References Cited

U.S. PATENT DOCUMENTS 3,171,770 A     3/1965  Biekart et al.
3,223,145 A  *  12/1965  Templeton ............ C07C 273/16
                                                                159/47.2
(Continued)

FOREIGN PATENT DOCUMENTS

EP     752416     1/1997
GB     1113828    5/1968
(Continued)

OTHER PUBLICATIONS

Wood ("Characterization of Flash Crystallization Process Using PAT" AIChE 2010 Annual Meeting Presentation Abstract, p. 1-2, originally presented on Nov. 9, 2010).*

(Continued)

*Primary Examiner* — Fereydoun G Sajjadi
*Assistant Examiner* — Amy C Bonaparte
(74) *Attorney, Agent, or Firm* — Morrison & Foerster LLP (57) ABSTRACT

Disclosed is a method for urea finishing. A urea solution is subjected to crystallization and, other than in conventional processes, the urea crystals are shaped by exerting mechanical force onto them. Thus, the conventional prilling or granulation finishing steps can be avoided, and so are the corresponding emissions of ammonia and/or dust. The crystallization comprises a flash crystallization. The invention also pertains to the urea particles obtainable by the process, to a urea plant, and to a method of modifying an existing urea plant.

6 Claims, 4 Drawing Sheets

(51) Int. Cl.
  *B01J 2/22* (2006.01)
  *B01J 2/30* (2006.01)
  *B29C 43/00* (2006.01)
  *C05C 9/02* (2006.01)
  *C05C 9/00* (2006.01)
  *B29K 75/00* (2006.01)

(52) U.S. Cl.
  CPC ........ *C07C 273/14* (2013.01); *B29K 2075/02* (2013.01); *C05C 9/005* (2013.01); *C05C 9/02* (2013.01); *Y10T 29/49716* (2015.01)

(58) Field of Classification Search
  CPC ... C07C 273/14; C07C 273/16; C07C 273/02; C05C 9/005
  USPC ............. 264/6, 319, 320, 325, 330, 299, 15; 29/401.1; 564/73
  See application file for complete search history.

(56) References Cited

U.S. PATENT DOCUMENTS

| | | | |
|---|---|---|---|
| 3,232,984 A | 2/1966 | Finneran | |
| 3,356,723 A | 12/1967 | Kaasenbrood | |
| 3,470,115 A * | 9/1969 | MacGregor | C08J 3/14 521/133 |
| 3,585,237 A | 6/1971 | Miller et al. | |
| 3,683,057 A | 8/1972 | Fujii et al. | |
| 4,219,589 A | 8/1980 | Niks et al. | |
| 6,277,311 B1 * | 8/2001 | Eimer | C07C 273/02 264/117 |

FOREIGN PATENT DOCUMENTS

| | | |
|---|---|---|
| JP | 0920747 | 1/1997 |
| JP | 4225183 | 2/2009 |
| JP | 4539010 | 9/2010 |
| WO | WO 2009/121843 | * 10/2009 |

OTHER PUBLICATIONS

International Preliminary Report on Patentability for PCT/NL2012/050715, dated Feb. 10, 2014, 9 pages.
Database WPI, accession No. 1984-174774 (1984).
International Search Report for PCT/NL2012/050715, dated Jan. 22, 2013, 5 pages.
Rijckaert and Biermans, "An Alternative for Concentrating an Urea Solution: Flash Evaporation", Fertilizer Focus (1997) pp. 94-96.

* cited by examiner

UREA FINISHING METHOD

CROSS-REFERENCE TO RELATED APPLICATIONS

This application is the national phase of PCT application PCT/NL2012/050715 having an international filing date of 12 Oct. 2012, which claims benefit of European application No. 11185307.3, filed 14 Oct. 2011. The contents of the above patent applications are incorporated by reference herein in their entirety.

FIELD OF THE INVENTION

The invention is in the field of urea production, and particularly pertains to urea finishing. The invention also pertains to the removal of ammonia from the off-gas of a finishing section of a urea production plant.

BACKGROUND OF THE INVENTION

Urea Synthesis

Urea is generally produced from ammonia and carbon dioxide. It can be prepared by introducing an ammonia excess together with carbon dioxide at a pressure between 12 and 40 MPa and at a temperature between 150° C. and 250° C. into a urea synthesis zone. The resulting urea formation can be presented best in the form of two consecutive reaction steps, in the first step ammonium carbamate being formed according to the exothermic reaction:

after which the ammonium carbamate formed is dehydrated in the second step to give urea according to the endothermic equilibrium reaction:

The extent to which these reactions take place depends among other things on the temperature and the ammonia excess used. The reaction product obtained in a urea synthesis solution substantially consists of urea, water, unbound ammonia and ammonium carbamate. The ammonium carbamate and the ammonia are removed from the solution and are generally returned to the urea synthesis zone. In addition to the above-mentioned solution in the urea synthesis zone, a gas mixture is formed which consists of unconverted ammonia and carbon dioxide together with inert gases, the so called reactor off-gas. The urea synthesis section may comprise separate zones for the formation of ammonium carbamate and urea. These zones may also be combined in a single apparatus.

In a urea stripping plant the decomposition of the ammonium carbamate that has not been converted into urea and the expulsion of the usual ammonia excess largely takes place at a pressure that is essentially almost equal to the pressure in the synthesis reactor. This decomposition and expulsion take place in one or more stripper(s) installed downstream of the reactor, possibly with the aid of a stripping gas such as, for example, carbon dioxide and/or ammonia, and with the addition of heat. It is also possible to apply thermal stripping. Thermal stripping means that use is made exclusively of the supply of heat to decompose ammonium carbamate and remove the ammonia and carbon dioxide present from the urea solution. The gas stream leaving a stripper contains ammonia and carbon dioxide which are condensed in a high-pressure condenser and then returned to the urea synthesis zone.

In a urea stripping plant the synthesis zone is operated at a temperature of 160-240° C. and preferably at a temperature of 170-220° C. The pressure in the synthesis reactor is 12-21 MPa, preferably 12.5-20 MPa. The ammonia to carbon dioxide molar ratio (N/C ratio) in the urea synthesis zone of a stripping plant lies usually in between 2.2 and 5 and preferably between 2.5 and 4.5 mol/mol. The synthesis zone can be carried out in a single reactor or in a plurality of reactors arranged in parallel or series.

After the stripping treatment, the pressure of the stripped urea solution is reduced in a urea recovery section. In a recovery section the non-converted ammonia and carbon dioxide in the urea solution is separated from the urea and water solution. A recovery section comprises usually a heater, a liquid/gas separation section and a condenser. The urea solution entering a recovery section is heated to vaporize the volatile components ammonia and carbon dioxide from that solution. The heating agent used in the heater is usually steam. The formed vapor in said heater is separated from the aqueous urea solution in the liquid/gas whereafter said vapor is condensed in the condenser to form a carbamate solution. The released condensation heat is usually dissipated in cooling water. The formed carbamate solution in that recovery section operated at a lower pressure than the pressure in the synthesis section is preferably returned to the urea synthesis section operating at synthesis pressure. The recovery section is generally a single section or can be a plurality of recovery sections arranged in series.

Urea Finishing

Today's urea production involves relatively clean processes, particularly low in the emission of urea dust and ammonia. However, besides the chemical synthesis of urea, the production of urea on a commercial scale requires that the urea be presented in a suitable solid, particulate form. To this end, urea production involves a finishing step in which a urea melt is brought into the desired particulate form, generally involving any one of prilling, granulation, and pelletizing.

Prilling used to be the most common method, in which the urea melt is distributed in a prilling tower and the droplets solidify as they fall down. However, the end-product is often desired to have a larger diameter and higher crushing strength than the one resulting from the prilling technique. These drawbacks led to the development of the fluidized bed granulation technique, where the urea melt is sprayed on granules that grow in size as the process continues. Prior to the injection in the granulator, formaldehyde is added to prevent caking and to give strength to the end-product.

The air that leaves the finishing section contains urea dust and ammonia. The latter is particularly caused by an unwanted side-reaction in the finishing step, viz. the formation of biuret, i.e. a dimerization of urea, with release of ammonia. Another side-reaction that may occur is hydrolysis of urea, again with release of ammonia. Thus, despite the relatively clean nature of the urea synthesis, the commercial production of urea inevitably goes with the formation of ammonia. This ammonia is normally emitted through the off-gas of the finishing section of a urea plant.

The concentration of urea takes usually place at high temperatures and sub-atmospheric pressures. Usually concentration of the urea solution to the desired moisture content in the anhydrous urea melt takes place in a concentration section comprising one or a sequence of one or more concentrators in series.

Usually the sub-atmospheric pressure needed to concentrate the urea solution to the desired pressures in the concentrators is done by a combination of cooling down the released gases by cooling water and by using steam as a driving force for an ejector to create the sub-atmospheric pressure in the concentrator. Alternatively in certain urea concentrators the sub-atmospheric pressure is created by the application of vacuum pumps.

The concentrator comprises usually a shell and tube heat exchanger and a gas to liquid separator. The urea solution is subjected to the tube side of the heat exchanger and the heating agent, necessary to heat said solution, is subjected to the shell side of that heat exchanger. The heating agent can be process vapor from the above mentioned urea process, hot water or steam. The urea solution phase and the formed vapor phase leaving said heat exchanger is separated in said gas to liquid separator.

The urea melt leaving the concentration is usually conveyed by a pump to the urea finishing section. The urea finishing sections usually used in urea plants for producing the urea end product are urea granulation finishing and urea prilling finishing.

For urea granulation finishing the desired urea concentration in the urea melt to the granulator is in between 95 and 99% by weight. The urea concentration in the urea melt sent to prilling finishing amounts in between 99.6 and 99.9% by weight. The urea melt sent to the finishing section comprises urea, water and small amounts of ammonia. The ammonia concentration in the urea melt sent to said urea finishing section amounts in between 100 and 900 ppm by weight.

The vapor released in the concentrators comprises ammonia, carbon dioxide and water. Said vapor is condensed in a condenser. The heat of condensation is usually dissipated in cooling water.

In another background method, the urea solution leaving the recovery section is subjected to a crystallization section. Crystallization sections are usually used when urea end products are needed that comprise a biuret content smaller than 0.5% by weight. A urea solution is subjected to a crystallizer. In the crystallizer usually operated at sub-atmospheric pressure, urea crystallizes partly. The formed vapor in the crystallizer is condensed in condensers while the urea solution including the formed urea crystals leaving the crystallizer is subjected to a liquid to solid separator. In this liquid to solid separator the bulk of solution is separated from the urea crystals whereafter said crystals are subjected to a centrifuge. In the centrifuge the urea crystals are washed by using a mother liquor comprising a urea water solution in which the biuret content amounts in between 1 and 10% by weight.

The liquid phase is furthermore separated from said crystals whereafter the urea crystals are transported to a re-melter to form a concentrated urea melt at a concentration in between 99.5 and 99.9% by weight that is subjected to the urea finishing section.

In the urea finishing section according prilling a substantially anhydrous urea melt is sprayed from the top of a prilling column in a rising stream of air of ambient temperature in which the droplets solidify to form so-called prills. The crystallization heat to solidify the urea droplets is released by this rising air flow.

The urea melt that is delivered to the fluidized bed of a urea granulation section as used for urea finishing section comprises, apart from urea and water also ammonia. The water present in the urea melt evaporates to a large extent during fluid-bed granulation of urea. Furthermore the urea melt is solidified. The released crystallization heat is in general removed by the air used for keeping the bed fluidized.

By the crystallization of the urea melt, small particles of the formed solidified urea escapes the prilling tower or fluid bed. These small particles are characterized as urea dust with a particle size in between 0.1 and 100 μm dependent of the finishing technology used. These particles leave the finishing by the discharged air flow. Because large amounts of air are used in the described finishing technologies, intense effective dedusting systems are needed to remove said particles from said air flow. Said dedusting systems need high investments and high energy consumptions.

Besides the dust formation in said urea finishing sections a large part of the dissolved ammonia in the urea melt sent to said finishing, is liberated and leaves said finishing section by the discharged air flow too. Dependent of the amount of air used in said finishing section, the ammonia concentration in the discharged air flow varies in between 50 to 150 mg per $m^3$ air.

Environmentally it is not acceptable anymore to sent said formed ammonia and urea dust in the discharged air flow into the atmosphere. Known technologies to remove the ammonia from that air flow, such as acid washing, have the disadvantages that they need high investment cost and the product to be formed by such an acid washing system have to be processed.

SUMMARY OF THE INVENTION

In order to better address one or more of the foregoing desires, the invention, in one aspect, provides a process for the production of urea particles from an aqueous urea solution, comprising a crystallization step, wherein the solution is subjected to a crystallization step, comprising flashing, preferably dry flashing, the urea solution so as to obtain a solid crystallized urea containing product and an ammonia and water containing vapor and subsequently a shaping step, wherein, the shaping step comprises exerting mechanical force on the urea crystals.

The invention also provides a process for the production of urea particles from an aqueous urea solution, comprising a crystallization step, wherein the crystallization step comprises flashing the urea solution at a pressure of from 1 to 30 kPa, and preferably of from 1 to 20 kPa so as to obtain a solid crystallized urea containing product and an ammonia and water containing vapor, and subsequently a shaping step, wherein the shaping step comprises exerting mechanical force on the urea crystals.

In yet another aspect, the invention provides the use of a compactor for the shaping of urea particles, wherein urea crystals obtained by a process of the invention, are pressed into a mold.

In a still further aspect, the invention presents a urea plant comprising a urea synthesis section, a recovery section, and a finishing section, wherein the recovery section comprises a device suitable for crystallizing urea from a solution, and the finishing section comprises a device suitable for exerting mechanical force on urea crystals.

In another aspect, the invention is a method of modifying an existing urea plant so as to reduce emissions of ammonia and dust therefrom, the method comprising adding to the plant a device suitable for crystallizing urea from a solution, and a device suitable for exerting mechanical force on urea crystals.

In a further aspect, the invention provides a method for increasing the plant capacity of a urea plant by increasing the capacity of a finishing section of said plant, the method comprising adding as a parallel finishing section a device suitable for crystallizing urea from a solution, and a device suitable for exerting mechanical force on urea crystals.

DETAILED DESCRIPTION OF THE INVENTION

In a general sense, the invention is based on the judicious insight that the provision of urea crystals can serve to avoid the conventional urea finishing techniques of prilling or granulation. Particularly, the invention is based on the direct use, i.e. without the conventional melt-processing, of urea crystals, to obtain shaped particles by mechanical force.

The process of the invention, as one its advantages avoids such steps as are prone to releasing ammonia and dust into the atmosphere. Thus, in marked contrast with the prilling or granulating steps according to conventional processing, the process of the invention does not require additional measures to reduce the release of ammonia and urea dust.

To this end, urea crystals are provided to an alternative finishing section according to the invention, wherein mechanical forces are exerted onto the crystals. Whilst the source of the crystals is not critical for the conducting of the shaping step, the advantages of the invention are enjoyed optimally in the event that the crystallization is conducted by subjecting a urea solution to sub-atmospheric conditions so as to allow the spontaneous formation of urea crystals. Preferably, prior to the crystallization step, the solution is concentrated so as to have to a urea concentration of 50% to 99% by weight of urea and biuret, and preferably of from 60% to 98% by weight. To improve the product quality with respect to crushing strength, formaldehyde or urea formaldehyde can be added to the urea solution subjected to the crystallization step.

Without wishing to be bound by theory, the present inventor believes that the crystallization step, wherein a urea solution is subjected to sub-atmospheric conditions, leads to an expansion of the urea solution, as a result of which spontaneously urea crystals are formed, and the remaining components in the urea solution like water and small amounts of ammonia evaporate. As a result, the formed ammonia concentration and dust formation released into the atmosphere is negligible, in the sense that this is less than 50 mg per $m^3$ for either of these components.

Thus, the invention provides an unexpected advantage associated with the direct use of the formed urea crystals, in shaping urea particles. According to the invention, this is done by exerting a mechanical force onto the crystallized particles. Thus, in accordance with the invention, a novel urea finishing results wherein urea crystals are shaped into pellets or flakes by using mechanical forces preferably by pressing, i.e. wherein the mechanical force is exerted onto the urea crystals by means of compression forces. Preferred examples of said alternative urea finishing section are pelletizers, compactors or flakers. In a preferred embodiment, the shaping is carried out in a compactor wherein the shaping involves pressing the urea crystals into a mold.

The formed urea product by said alternative urea finishing can be made in any size and form. Preferably the urea end product shape is spherical and the diameter is in between 0.3 and 20 millimeter. Preferably the diameter of the urea particles (i.e. the urea end product) is in between 1.0 and 10.0 millimeter. In connection herewith, the invention also pertains to urea particles obtainable by a process according to any one of the embodiments herein described.

The crystallization process in accordance with the invention, can be conducted on the basis of any urea synthesis process.

A frequently used process for the preparation of urea according to a stripping process is the carbon dioxide stripping process as for example described in Ullmann's Encyclopedia of Industrial Chemistry, Vol. A27, 1996, pp 333-350. In this process, the synthesis section is followed by one or more recovery sections. The synthesis section comprises a reactor, a stripper, a condenser and a scrubber in which the operating pressure is in between 12 and 18 MPa and preferably in between 13 and 16 MPa. In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, steam is added to heat the solution. The urea solution leaves the heat exchanger at the bottom part, while the vapor phase leaves the stripper at the top part. The vapor leaving said stripper contains ammonia, carbon dioxide and a small amount of water. Said vapor is condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The heat released by the exothermic carbamate condensation reaction in said condenser is usually used to produce steam that is used in a downstream urea processing section for heating and concentrating the urea solution. Since a certain liquid residence time is created in a submerged type condenser, a part of the urea reaction takes already place in said condenser. The formed solution, containing condensed ammonia, carbon dioxide, water and urea together with the non-condensed ammonia, carbon dioxide and inert vapor is sent to the reactor. In the reactor the above mentioned reaction from carbamate to urea approaches the equilibrium. The ammonia to carbon dioxide molar ratio in the urea solution leaving the reactor is generally in between 2.5 and 4 mol/mol. It is also possible that the condenser and the reactor are combined in one piece of equipment. An example of this piece of equipment as described in Ullmann's Encyclopedia of Industrial Chemistry, Vol. A27, 1996, pp 333-350. The formed urea solution leaving the urea reactor is supplied to the stripper and the inert vapor containing non-condensed ammonia and carbon dioxide is sent to a scrubbing section operating at a similar pressure as the reactor. In that scrubbing section the ammonia and carbon dioxide is scrubbed from the inert vapor. The formed carbamate solution from the downstream recovery system is used as absorbent in that scrubbing section. The urea solution leaving the stripper in this synthesis section requires a urea concentration of at least 45% by weight and preferably at least 50% by weight to be treated in one single recovery system downstream the stripper. The recovery section comprises a heater, a liquid/gas separator and a condenser. The pressure in this recovery section is between 200 to 600 kPa. In the heater of the recovery section the bulk of ammonia and carbon dioxide is separated from the urea and water phase by heating the urea solution. Usually steam is used as heating agent. The urea and water phase, contains a small amount of dissolved ammonia and carbon dioxide that leaves the recovery section and is sent to a downstream urea processing section where the urea solution is concentrated by evaporating the water from said solution.

The invention is not limited to any particular urea production process. Other processes and plants include those that are based on technology such as the HEC process developed by Urea Casale, the ACES process developed by Toyo Engineering Corporation and the process developed by Snamprogetti. All of these processes, and others, may be used preceding the urea finishing method of the invention.

In the invention, a urea solution obtained in any urea synthesis process, is subjected to a crystallization step by subjecting the urea solution to expansion by being brought under conditions of sub-atmospheric pressure, i.e by flashing. This type of crystallization is very suitable with a view to commercial scale processing. Preferably the crystallization step comprises flashing the urea solution at a pressure of from 1 to 60 kPa, and preferably of from 2 to 50 kPa, so as to spontaneously obtain a solid urea product.

In one embodiment hereof, the urea solution formed in a recovery section from a urea plant is sent to a crystallizer. The crystallizer is operated at a pressure in between 10 and 60 kPa, preferably between 20 and 50 kPa, and spontaneously urea crystals are formed by the expansion. The formed vapor is subjected to condensers. The urea crystals including the left urea solution leaving the crystallizer is subjected to a liquid to solid separator where the bulk of urea solution is separated from the formed urea crystals. Said urea crystals leaving the liquid to solid separator are subjected to a centrifuge in which the left urea solution is further separated from said crystals. A mother liquor comprising an aqueous urea solution that comprises biuret can be added to the centrifuge in order to wash said crystals in order to obtain purified urea crystals comprising a biuret content in between 0.1 and 0.6% by weight only. The urea crystals leaving the centrifuge are further dried in a drying column whereafter the dried urea crystals comprising only about 0.1 to 0.6% by weight moisture and preferably comprising 0.1 to 0.4% by weight of moisture is subjected to said urea shaping device.

The released vapor after the expansion of the urea solution is increased in pressure and transported to a condenser. Preferably a steam ejector or a vacuum pump is used for increasing the pressure. In the condenser the vapor comprising water and small amounts of impurity components like ammonia and carbon dioxide and inert, is condensed. Preferably cooling water is used for condensing said vapors. The non condensed vapors leaving the condenser are subjected to a steam ejector or a vacuum pump to increase pressure where after a further purification of these vapors take place. This can be done by again condensing these vapors at a higher pressure where after the left inert vapor is released into the atmosphere or is again purified in an inert purification unit as for example an absorber. The formed process condensate in the condensers is collected where after said process condensate is subjected to a process condensate purification in the urea plant.

In a preferred embodiment, the subjection of the urea solution to sub-atmospheric conditions is conducted by flashing the urea solution, i.e. removing liquid by evaporation under reduced pressure, so as to spontaneously obtain a solid urea product and an ammonia and water containing vapor. In a typical embodiment the flashing is conducted at a pressure of from 1 to 30 kPa, and preferably of from 1 to 20 kPa, Flashing can be done in a flashing device, such as a dry flasher. A dry flasher is characterized in that a liquid stream is converted by crystallization and evaporation into substantially a solid and a vapour. In a dry flasher the process conditions are selected such that the amount of liquid remaining is substantially nil. This allows for a clean separation of the gas and the solids without substantial sticking and fouling. Another advantage of the dry flashing is that due to the absence of a slurry, no solid liquid separation such as a centrifuge, nor a re-melter is necessary. This allows a significantly simpler process scheme. Such a dry flasher is a vessel that operates at a pressure in between 1 and 30 kPa and preferably at a pressure in between 2 and 10 kPa. In said dry flasher the urea solution is distributed by a liquid distributer. By the expansion the urea and biuret crystallizes spontaneously in a solid and the remaining components comprising water, ammonia and small amounts of carbon dioxide evaporate.

The particle size of the obtained solid urea product by adiabatic flashing is in the range of from 0.1 µm to 1000 µm, preferably of from 1 µm to 800 µm.

The invention also pertains to a urea plant. The plant of the invention comprises a urea synthesis section, a recovery section, and a finishing section, wherein the recovery section comprises a device suitable for crystallizing urea from a solution, and the finishing section comprises a device suitable for exerting mechanical force on urea crystals. Devices suitable for crystallization can be a conventional crystallization vessel, or an adiabatic flash device as indicated above.

In a particularly interesting embodiment, the invention can also be put to use in modifying existing urea plants. Such existing urea plants, which will normally have a finishing section based on prilling or granulation, can be modified by adding equipment suitable for conducting the crystallization and shaping steps of the above-described methods. By thus substituting the conventional finishing section by the new equipment of the invention, the emissions of ammonia and/or dust normally associated with prilling or granulation can be reduced, or even avoided, without additional measures. Thus, the invention includes a method of modifying an existing urea plant so as to reduce emissions of ammonia and dust therefrom, the method comprising adding to the plant a device suitable for crystallizing urea from a solution, and a device suitable for exerting mechanical force on urea crystals.

In another interesting embodiment, the invention can be used in order to increase the capacity of an existing urea plant. The finishing section can sometimes be a bottleneck in optimizing the capacity of a plant. Since traditional finishing sections, particularly in the cases of prilling towers, are relative large, it is not always possible to expand the finishing section of an existing plant. Also, the expansion of the finishing section will normally go with an at least proportional increase in emissions of ammonia gas and urea dust. By virtue of the present invention, it is now possible to increase the capacity of an existing urea plant by increasing the capacity of a finishing section of such a plant. This can be carried through by adding, parallel to the existing finishing section, a finishing section according to the invention, i.e., a device suitable for crystallizing urea from a solution, and a device suitable for exerting mechanical force on urea crystals. In accordance with the invention, the problems associated with increasing the capacity of the finishing section are addressed, since the parallel alternative finishing section will go with reduced, or even avoided, emissions of gaseous ammonia and urea dust. Thus, with the capacity increased, the emissions per quantity of produced urea are in fact reduced. Also, the addition of the parallel finishing section of the invention addresses the normal challenges associated with increasing the already large finishing section, as a new or enlarged prilling tower is not needed.

Figure 2:
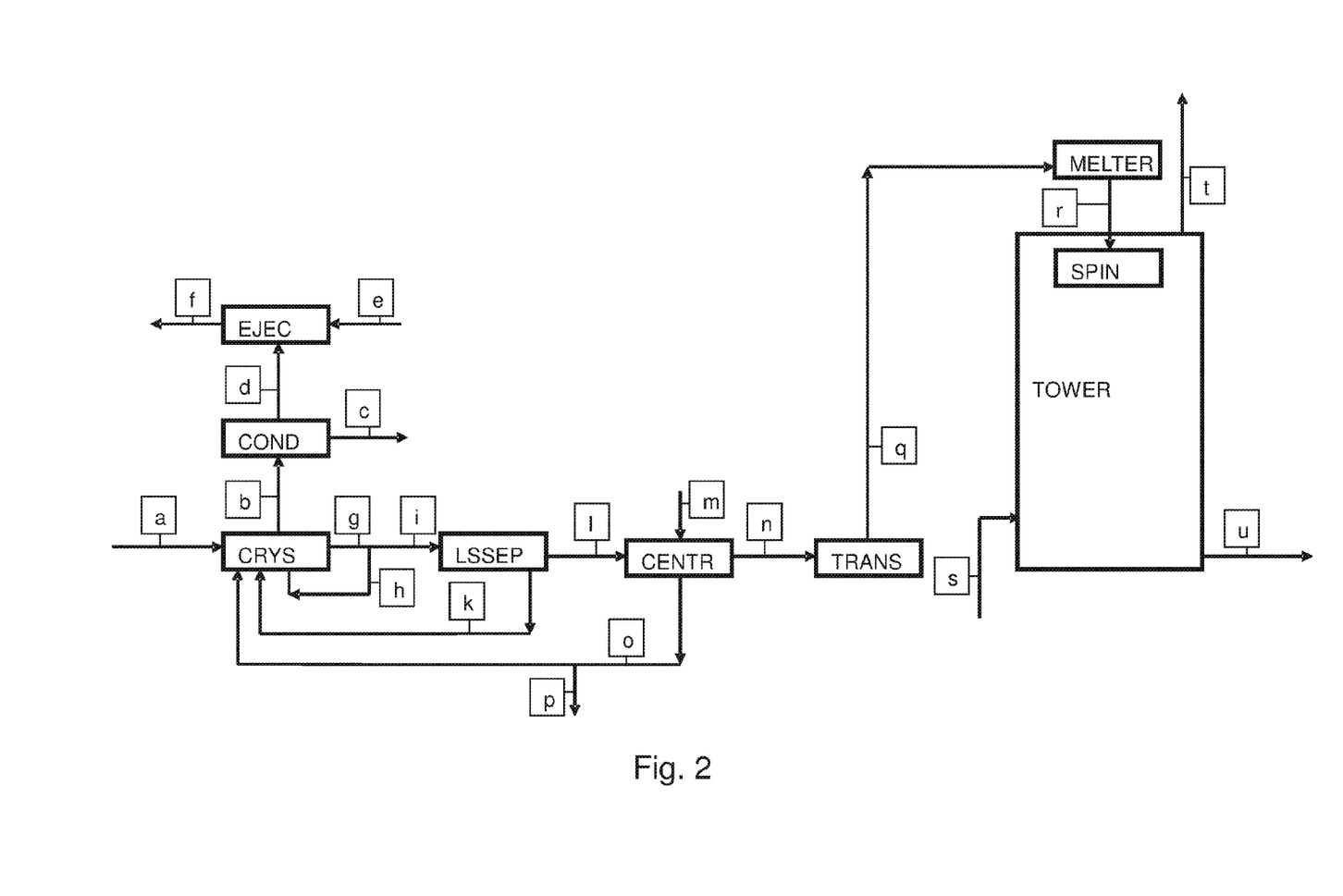
FIG. 2 shows another exemplified scheme of a conventional process, wherein a urea solution from a urea plant is subjected to a crystallization section to obtain a urea melt containing low biuret content in between 0.1 and 0.5% by weight.
Figure 3:
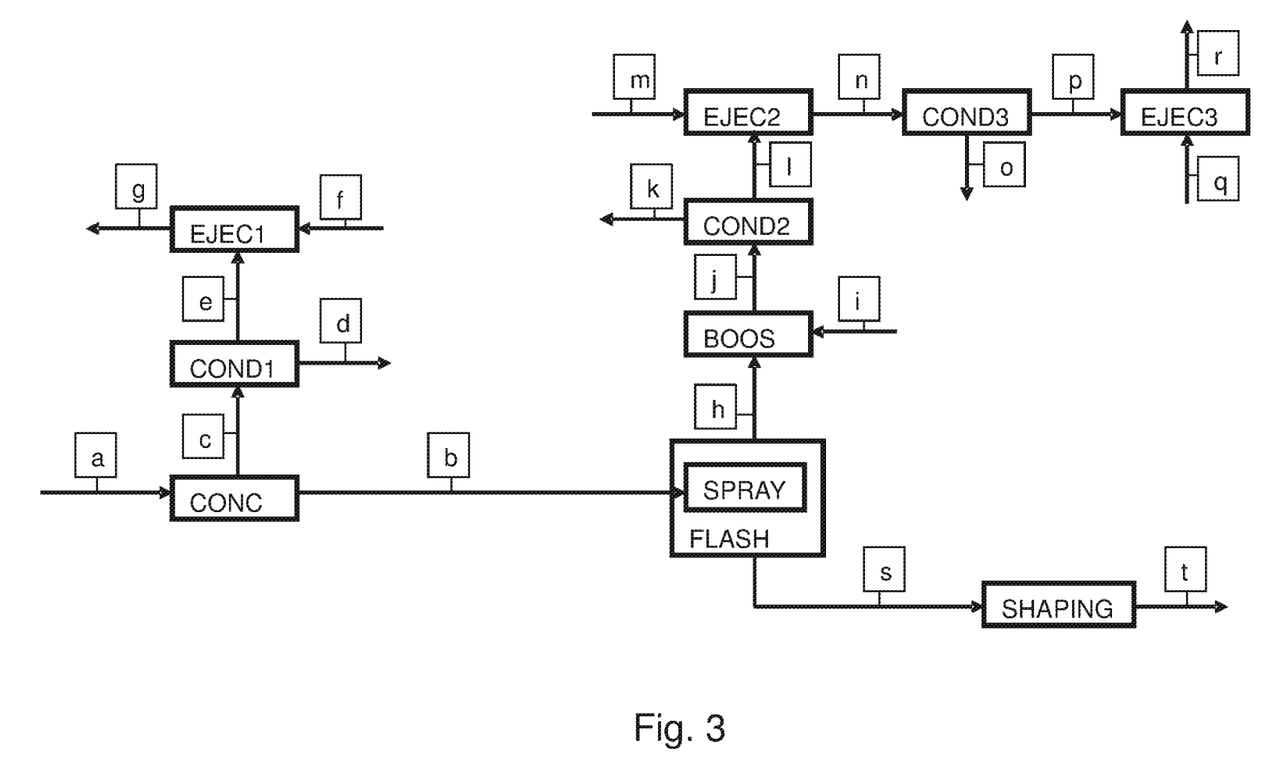
FIG. 3 is a scheme showing an example according to the invention.
Figure 4:
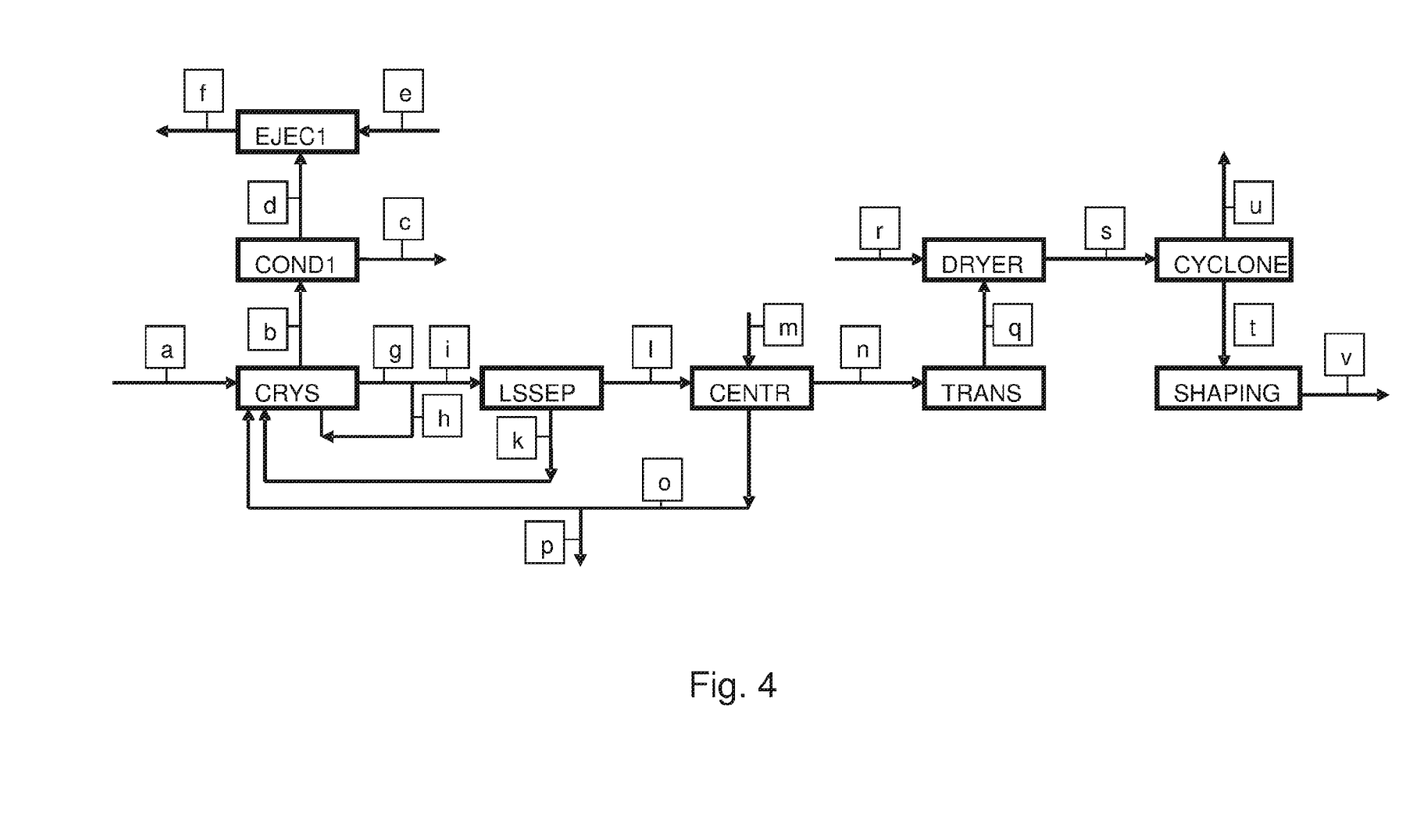
FIG. 4 is a schematic representation of another example according to the invention.

In accordance with the invention, it is possible to avoid or minimize the ammonia and urea dust emissions into the atmosphere via the alternative finishing section of the urea to an end product to values less than 0.3 kg urea per ton of produced urea end product. For ammonia the amount of emission shall preferably not exceed 0.1 kg per ton of produced urea end product The invention will hereinafter be further illustrated with reference to the following, non-limiting examples. The state of the art is illustrated in FIGS. 1 and 2, while two embodiments of the invention are shown in FIGS. 3 and 4.

Figure 1:
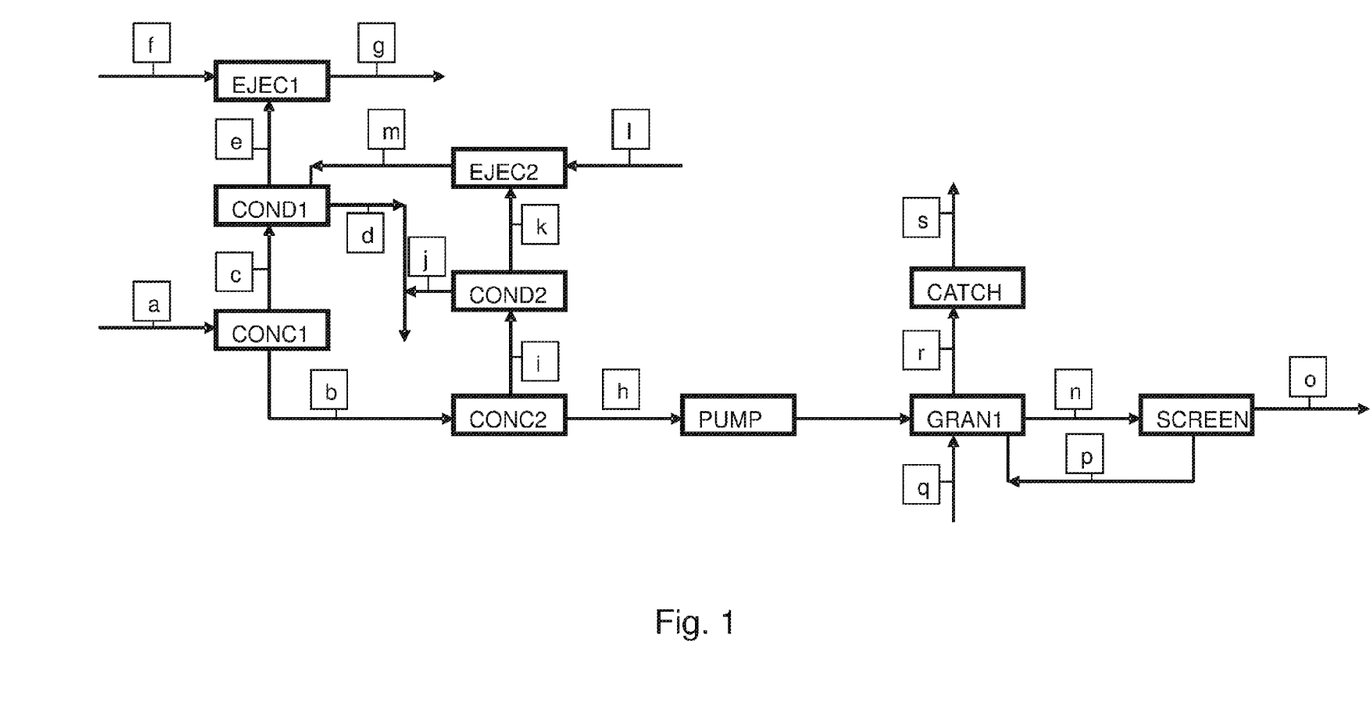
FIG. 1 is a schematic representation of a typical sequence for concentrating a urea solution to a urea melt where after the urea melt is subjected to a typical granulation unit as urea finishing section as known from the prior art.

FIG. 1 shows a typical sequence for concentrating a urea solution to a urea melt where after the urea melt is subjected to a typical granulation unit as urea finishing section as known from the prior art.

A urea solution from a recirculation section of a urea plant with a typical concentration in between 50 and 80% by weight and a typical temperature in between 60 and 90° C. is added to a concentrator (CONC1) via line (a). The concentrator (CONC1) is a shell and tube heat exchanger and the urea solution is subjected to the tube side of said concentrator. At the shell side of said concentrator steam is added to heat the solution and to evaporate the volatile water fraction. The urea solution leaving the concentrator (CONC1) via line (b) has typically a temperature of 125 to 135° C. and is concentrated to typically 93 to 96% by weight of urea. The pressure in said concentrator is sub-atmospheric and typically in between 20 to 50 kPa. The formed vapor comprising water and small amounts of ammonia and carbon dioxide is discharging said concentrator via line (c). Said vapor is condensed in a condenser (COND1) and leaves said condenser as process condensate via line (d). Non-condensed vapor is leaving said condenser via line (e) and is subjected to an ejector (EJEC1) to increase the pressure to atmospheric pressure. The driving force for said ejector is usually steam via line (f). The steam together with the non-condensed vapor leaves said ejector via line (g) and can be subjected to the atmosphere but preferably is purified in the urea plant itself.

The urea solution leaving the concentrator (CONC1) via line (b) is subjected to a second concentrator (CONC2). Also this concentrator (CONC2) is typically a shell and tube heat exchanger where the urea solution is subjected to the tube side of said heat exchanger while steam is added to the shell side to heat and vaporize the volatile water fraction at sub atmospheric pressure that is typically in between 1 to 30 kPa and preferable in between 2 and 20 kPa. The temperature of the urea melt leaving said concentrator via line (h) is typically in between 136 and 145° C. and comprises typically a concentration in between 97.5 to 99% by weight of urea and biuret. The formed vapor formed by the concentration of said solution to said melt comprising water, ammonia and some entrained urea, is subjected to a condenser (COND2) via line (i). In said condenser (COND2) the bulk of vapor is condensed to form process condensate by the aid of cooling water. The formed process condensate leaves said condenser via line (j). The non-condensed vapor leaving said condenser (COND2) comprising inert, water and small amounts of ammonia via line (k) is subjected to a steam ejector (EJEC2). Said ejector is driven by steam via line (l) and increases the pressure of said inert vapor that leaves said ejector via line (m) to the condenser (COND1).

The urea solution leaving said concentrator (CONC2) via line (h) is sent by a pump (PUMP) to a fluid bed granulator (GRAN1) as urea finishing section. An additive such as formaldehyde or urea formaldehyde solution can be added to said urea solution. Ordinary fluid-bed granulation processes comprises a granulator (GRAN1) in which urea melt is fed to a fluid bed of solid urea nuclei upon the nuclei grow by solidification to obtain urea granules. The obtained granules have a certain size distribution when leaving said granulator. These granules are usually cooled where after these obtained granules are sent to a size classification unit via line (n) and in most cases this classification unit comprises a number of screens (SCREEN). By that classification unit the fines and the coarse material is separated from the remaining granules that is after a secondary cooling unit sent as product to a storage or transportation section via line (o).

The coarse material fraction is crushed to a certain granule size and recycled together with the fines fraction via line (p) into the granulator (GRAN1) where it acts as nuclei.

Air is supplied to the fluid bed granulator via line (q) to keep the solid nuclei in said granulator fluidized. The air discharging said granulator via line (r) comprises ammonia and urea dust and has to be treated in a urea dust catcher (CATCH) before the air is discharged into the atmosphere via line (s). Dependent of the amount of air supplied as air needed for fluidization in the fluid bed granulator (GRAN1) by line (q), the ammonia and dust emission in the air exhausted into the atmosphere via line (s) is typically in between 50 and 200 mg per normal $m^3$ respectively in between 20 and 50 mg per normal $m^3$. This corresponds for the ammonia emission in between 0.5 and 1.5 kg per produced ton of urea end product and for the urea dust emission in between 0.2 and 1 kg per produced ton of urea end product.

FIG. 2 shows another example of a urea solution from a urea plant that is subjected to a crystallization section to obtain a urea melt containing low biuret content in between 0.1 and 0.5% by weight.

A urea solution from a recirculation section of a urea plant with a typical concentration in between 50 and 80% by weight and a temperature in between 60 and 90° C. is added to a crystallizer (CRYS) via line (a). The pressure in the crystallizer is in between 10 and 50 kPa. By the expansion of the urea solution spontaneously urea crystals are formed to a slurry comprising a mixture of solid urea crystals in a urea solution. The amount of urea crystals in said slurry is in between 2 and 30% by weight. The formed vapor comprising water, ammonia and small amounts of carbon dioxide in said crystallizer (CRYS) is discharged to a to a condenser (COND) via line (b). In said condenser said vapor is condensed and leaves said condenser via line (c). The inert vapor comprising some water, ammonia and traces of non-condensed other components, leaves said condenser via line (d) to an ejector (EJEC) to increase the pressure to about atmospheric pressure. The driving force for said ejector is usually steam via line (e). The steam together with said non-condensed inert vapor leaves said ejector via line (f) to the atmosphere or is further purified elsewhere in the urea plant before releasing into the atmosphere.

The slurry comprising said urea crystals and urea solution leaving the crystallizer (CRYS) via line (g) is partly recycled to said crystallizer via line (h) and the remaining discharged to a solid to liquid separator (LSSEP) via line (i). In said liquid to solid separator the bulk of urea solution is separated from the urea crystals. Said urea solution is recycled to the crystallizer (CRYS) via line (k). The urea crystals leaving the liquid to solid separator (LSSEP) comprises still a considerable amount of urea solution (about 2 to 10% by weight) is subjected to a centrifuge (CENTR) via line (l). In said centrifuge a further separation of urea solution from the urea crystals takes place by using centrifugal forces. Washing liquid usually comprising urea, biuret, water and ammonia can be added to said centrifuge in order to reduce the biuret content in the urea crystals via line (m). The urea crystals leaves said centrifuge (CENTR) via line (n) to an urea crystal transportation (TRANS). The urea solution leaving said centrifuge via line (o) is recycled to the crystallizer (CRYS) and partly purged to the urea plant via line (p). The urea crystals leaving the urea crystal transportation (TRANS) is subjected via line (q) to a heat exchanger where the urea crystals are melted (MELTER). Usually steam is used as a heating agent for said heat exchanger (MELTER). When prilling is used as urea finishing section, the formed urea melt leaves said heat exchanger (MELTER) and is subjected to a melt distributor (SPIN) on top of a prilling tower (TOWER) via line (r) where the melt is distributed across the circumferential diameter from the top of said prilling tower in a rising stream of air of ambient temperature in which the formed droplets solidify to form so called prills.

In said prilling tower the air is added to said tower at the bottom via line (s) and leaves said tower at the top via line (t). The urea dust formed by the distribution, cooling down path of melt and solid prills is leaving said prilling tower together with the discharging air and amounts in between 0.7 and 1.5 kg per produced ton of urea end product. The ammonia in the urea melt supplied to the melt distributer (SPIN) leaves said prilling tower also together with the air at the top of said tower via line (u) and amounts in between 0.5 and 1 kg per produced ton of urea end product.

The urea end product (prills) discharge the prilling tower (TOWER) at the bottom via line (u).

FIG. 3 shows an example of the embodiment according to the invention.

A urea solution with a concentration of typically 50 to 80% by weight and a temperature of typically 60 to 90° C. is added to a concentrator (CONC) via line (a). The concentrator (CONC) is a shell and tube heat exchanger and the urea solution is subjected to the tube side of said concentrator. At the shell side of said concentrator steam is added to heat the solution and to evaporate the volatile water fraction. The urea solution leaving the concentrator (CONC) via line (b) has typically a temperature of 110 to 130° C. and is concentrated to 80 to 97% by weight of urea and preferably to a urea concentration of 85 and 95% by weight. The pressure in said concentrator is sub-atmospheric and typically in between 15 to 70 kPa and preferably in between 20 and 50 kPa. The formed vapor, comprising water and amounts of ammonia and carbon dioxide is discharging said concentrator via line (c). Said vapor is condensed in a condenser (COND1) and leaves said condenser as process condensate via line (d). Non-condensed vapor comprising inert, water, ammonia and carbon dioxide, leaves said condenser via line (e) and is subjected to an ejector (EJEC1) to increase the pressure to atmospheric pressure. The driving force for said ejector is usually steam via line (f). The steam together with the non-condensed vapor leaves said ejector via line (g) and can be subjected to the atmosphere but preferably is purified in the urea plant itself before releasing it into the atmosphere.

The urea solution leaving the concentrator (CONC) via line (b) is sent to a dry flasher (FLASH). Said dry flash is a vessel that operates at a pressure in between 1 and 30 kPa and preferably at a pressure in between 2 and 10 kPa. In said dry flasher the urea solution is distributed by a liquid distributer (SPRAY). By the expansion the urea and biuret crystallizes spontaneously in a solid and the remaining components comprising water, ammonia and small amounts of carbon dioxide evaporates. The formed vapor leaves the dry flasher (FLASH) via line (h) to a booster ejector (BOOS). The preferred driving force for said booster ejector is steam supply via line (i). The boosted vapor leaving said booster ejector via line (j) is subjected to a condenser (COND2). The formed process condensate, which may also contain small amounts of urea dust, leaves said condenser via line (k) and may be recycled into the process upstream of the concentrator (CONC) while the non-condensed vapor leaving said condenser via line (l) is subjected to an ejector (EJEC2). Also said ejector is driven by steam via line (m) and increases the pressure of the vapor leaving said ejector via line (n). This vapor is subjected to a next condenser (COND3) where the formed process condensate leaves said condenser via line (o) and the non-condensed inert vapor via line (p) is subjected to a next ejector (EJEC3). Also said ejector is driven by steam via line (q) and increases the pressure of the vapor discharging said ejector to atmospheric pressure. That inert vapor is sent via line (r) into the atmosphere or is preferably purified from ammonia elsewhere in the urea plant before releasing it into the atmosphere. The process condensate that leaves said condensers is collected and processed in the urea plant to become clean process condensate.

The formed solid urea particles in the dry flasher have a particle size in between 1 and 1000 μm, preferably in between 10 and 500 μm and are extracted from said dry flasher (FLASH) via line (s).

Known extractors to extract solid product from vacuum systems are for example but not limited to air lock rotary feeders, seal vessel with double valves and venture ejectors.

The extracted solid urea particles via line (s) are conveyed to the alternative urea finishing section comprising a urea shaping device (SHAPING). In said urea shaping device the urea particles are subjected in a mold and by using mechanical forces it is pressed to the desired end product shape. Preferably the urea end product shape is spherical and the diameter is in between 0.3 and 10 millimeters. By shaping the urea end product by such a urea shaping device, the ammonia released into the atmosphere according such urea finishing technology is negligible. If urea dust is formed, the amount of formed urea dust does not exceed 0.3 kg per ton of produced product and the particle size of such dust is larger than 10 μm and thus easy to catch in ordinary de-dusting systems such as cyclones and wet washers. The urea end product leaves the urea shaping device (SHAPING) via line (t).

FIG. 4 shows another example of the embodiment according to the invention.

A urea solution from a recirculation section of a urea plant with a typical concentration in between 50 and 80% by weight and a temperature in between 60 and 90° C. is added to a crystallizer (CRYS) via line (a). The pressure in the crystallizer is in between 10 and 50 kPa. By the expansion of the urea solution spontaneously urea crystals are formed to a slurry comprising a mixture of solid urea crystals in a urea solution. The amount of urea crystals in said slurry is in between 2 and 30% by weight. The formed vapor comprising water, ammonia and small amounts of carbon dioxide in said crystallizer (CRYS) is discharged to a to a condenser (COND1) via line (b). In said condenser said vapor is condensed and leaves said condenser via line (c). The inert vapor comprising some water, ammonia and traces of non-condensed other components, leaves said condenser via line (d) to an ejector (EJEC1) to increase the pressure to about atmospheric pressure. The driving force for said ejector is usually steam via line (e). The steam together with said non-condensed inert vapor leaves said ejector via line (f) to the atmosphere or is further purified elsewhere in the urea plant before releasing into the atmosphere.

The slurry comprising said urea crystals and urea solution leaving the crystallizer (CRYS) via line (g) is partly recycled to said crystallizer via line (h) and the remaining discharged to a solid to liquid separator (LSSEP) via line (i). In said liquid to solid separator the bulk of urea solution is separated from the urea crystals. Said urea solution is recycled to the crystallizer (CRYS) via line (k). The urea crystals leaving the liquid to solid separator (LSSEP) comprises still a considerable amount of urea solution (about 2 to 10% by weight) is subjected to a centrifuge (CENTR) via line (l). In said centrifuge a further separation of urea solution from the urea crystals takes place by using centrifugal forces. Washing liquid usually comprising urea, biuret, water and ammonia can be added to said centrifuge in order to reduce the biuret content in the urea crystals via line (m). The urea crystals leave said centrifuge (CENTR) via line (n) to an urea crystal transportation (TRANS). The urea solution leaving said centrifuge via line (o) is recycled to the crystallizer (CRYS) and partly purged to the urea plant via line (p).

The urea crystals leaving the urea crystal transportation (TRANS) is subjected via line (q) to a urea crystal dryer (DRYER) in which the remaining urea solution is evaporated from the urea crystals. Hot dry air at a temperature of 100 to 150° C. via line (r) can be used and this air is also used for transporting the urea crystals to the alternative urea finishing section comprising a shaping device via line (s). The dry hot air via line (r) and the urea crystals via line (q) are preferably supplied to the bottom of the urea crystal dryer (DRYER) and discharged at the top of said dryer via line (s). The urea crystals are preferably separated from the air by the application of a cyclone (CYCLONE). The urea crystals are subjected via line (t) to urea shaping device (SHAPING) while the air leaves said cyclone via line (u). In said urea shaping device the urea crystals are subjected in a mold and by using mechanical forces the desired end product shape is obtained. Preferably the urea end product shape is spherical and the diameter is in between 0.3 and 10 millimeters. By shaping the urea end product by such a urea shaping device, the ammonia released into the atmosphere according such urea finishing technology is negligible. If urea dust is formed, the amount of formed urea dust does not exceed 0.3 kg per ton of produced product and the particle size of such dust is larger than 10 μm and thus easy to catch in ordinary de-dusting systems such as cyclones and wet washers.

The urea end product leaves the urea shaping device (SHAPING) via line (v).

The invention claimed is:

1. A process for the production of urea pellets or flakes from an aqueous urea solution comprising subjecting said aqueous urea solution to dry flashing so as to result in a product that contains substantially no liquids and which product consists essentially of solid urea particles and an ammonia and water containing vapor, followed by exerting mechanical force on the urea particles, thus producing said urea pellets or flakes;

wherein the urea pellets or flakes are of a size in the range of from 1 mm to 20 mm, and wherein the urea particles obtained by dry flashing are of a size between 10 and 500 μm;

the dry flashing is carried out at 2 to 10 kPa;

the dry flashing is adiabatic; and the aqueous urea solution has a urea concentration of 85 to 95% by weight.

2. The process of claim 1, wherein the mechanical force is exerted onto the urea particles by means of compression forces.

3. The process of claim 1, wherein said aqueous urea solution comprises formaldehyde or urea formaldehyde as an additive.

4. The process of claim 1, wherein the dry flashing comprises distributing the aqueous urea solution using a liquid distributor.

5. The process of claim 1 wherein said process further comprises extracting the urea particles from the dry flashing using a extractor for extracting solid products from vacuum systems, directly conveying said extracted urea particles to a urea shaping device, and subjecting the urea particles into a mold and pressing the urea particles into pellets or flakes.

6. The process of claim 1 which further comprises capturing any dust with a cyclone or wet washer from said exerting of mechanical force; wherein the mechanical force is exerted onto the urea particles by means of compression forces.

* * * * *